United States Patent [19]
Ullmark

[11] Patent Number: 5,385,566
[45] Date of Patent: Jan. 31, 1995

[54] DEVICE AND A METHOD FOR USE IN TRANSPLANTATION OF BONE TISSUE MATERIAL

[76] Inventor: Gösta Ullmark, Vallrundan 27, 818 33 Valbo, Sweden

[21] Appl. No.: 24,175

[22] Filed: Feb. 22, 1993

[30] Foreign Application Priority Data

Feb. 20, 1992 [SE] Sweden ................................ 9200501

[51] Int. Cl.⁶ ............................ A61F 2/36; A61F 5/04
[52] U.S. Cl. ......................................... 606/95; 606/94
[58] Field of Search ......................... 606/92, 93, 94, 95

[56] References Cited

U.S. PATENT DOCUMENTS

| | | | |
|---|---|---|---|
| 4,337,773 | 7/1982 | Poftopoulos et al. | 606/95 |
| 5,071,040 | 12/1991 | Laptewicz, Jr. | 606/93 |
| 5,078,746 | 1/1992 | Garner | 606/95 |
| 5,192,283 | 3/1993 | Ling et al. | 606/92 |

*Primary Examiner*—Stephen C. Pellegrino
*Assistant Examiner*—Sonya C. Harris
*Attorney, Agent, or Firm*—Browdy and Neimark

[57] ABSTRACT

A device and a method for use in transplantation of bone tissue material in a cavity (7) in bones (6) so as to give the cavity a desired shape with a required thickness of the bone material forming the wall of the cavity, is based on the use of a means (3) for compacting the bone tissue material (15) in the cavity. A guide pin (1) is adapted to be applied substantially centrally in the cavity (7). The compacting means (3) has an opening (10) for passage of the guide pin (1) so as to obtain guiding of the compacting means by the guide pin on movement of said means with respect thereto. The compacting means (3) has a jacket (12) delimiting an inner hollow space (13). The jacket (12) is provided with an opening (16) for allowing liquid to pass through the jacket and into the hollow space.

9 Claims, 2 Drawing Sheets

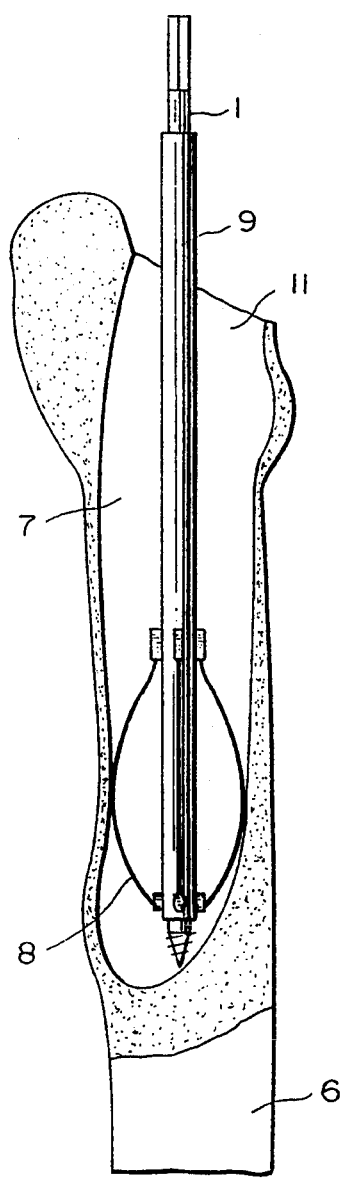
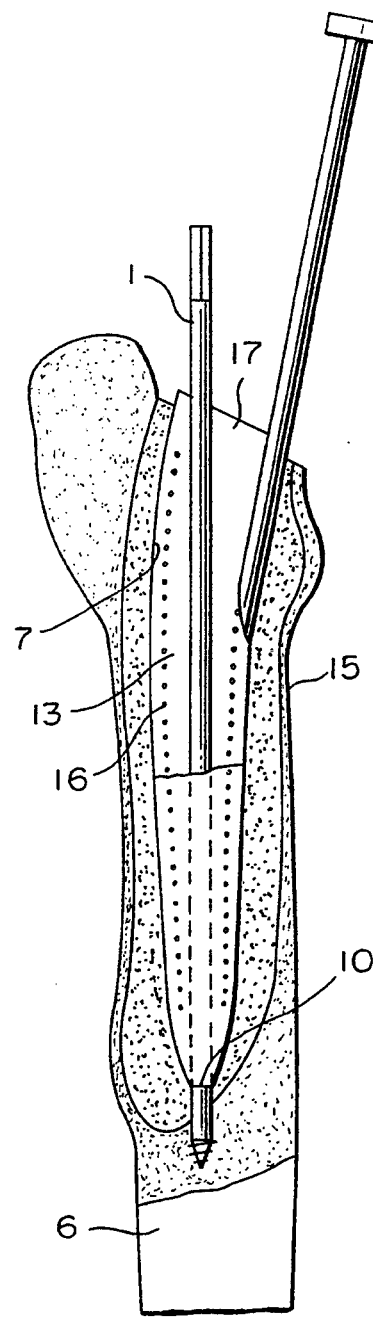
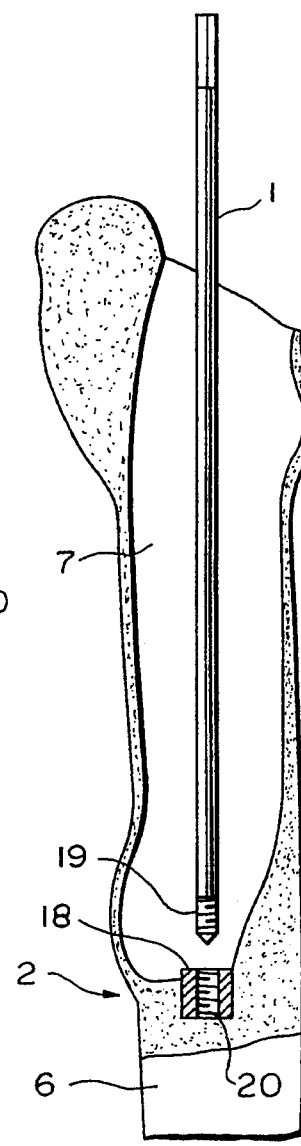
FIG. 5
FIG. 6
FIG. 7

DEVICE AND A METHOD FOR USE IN TRANSPLANTATION OF BONE TISSUE MATERIAL

FIELD OF THE INVENTION AND PRIOR ART

This invention relates to a device and a method for use in transplantation of bone tissue material in a cavity in bones so as to give the cavity a desired shape with a required thickness of the bone material forming the wall of the cavity. The invention is in the preferred case intended to be used as a pretreatment in such orthopaedic surgical operations in which a portion of a prosthesis shall be inserted into said cavity and be secured therein. Bone cement is then utilized for the securing between the prosthesis portion and the wall of the cavity defined by the bone tissue material.

A particularly preferred application of the invention relates to preparation of cavities in femurs so as to receive a portion of a hip joint prosthesis. However, it should be understood that the invention may be applied also in other cases where arbitrary prosthesis, for example joint or articulation prosthesis, are to be applied in a bone of the individual. It should be pointed out that said "bone" may be constituted by any member, such as an arm, of the musculoskeletal system of the patient.

When there is a need of a replacement of in particular hip joint prosthesises it is usually so that bone resorption has taken place in the femur where the stem portion of the prosthesis has been located. Accordingly, a large cavity with surrounding thin bone is left in the bone when the old prosthesis is removed, so that the support for a new prosthesis is bad. A first way to try to solve this problem is to use a longer prosthesis. A second way is to try to transplant bone so as to produce thicker bone walls around the cavity. The present invention is occupied with the second way.

A first conventional method to transplant bone inside the femur cavity has been to by hand place bone pieces at the places where they are desired, i.e. where the wall of the cavity is hazardously thin. This method is unreliable, since the bone piece may possibly not remain in the right place, and there is also a risk for entrance of bone cement between the bone piece and that part of the femur with which the bone piece shall grow together.

Another method developed recently consists in filling the cavity in the bone by a bone transplant consisting of a bone tissue material, in which bone tissue is present as a plurality of small pieces or particles, i.e. in a grinded or finely divided state. The bone tissue material is brought into a suitable consistency as paste or pulp. The bone tissue material contains then a suitable liquid. This liquid may comprise tissue liquid, such as blood. The liquid comprises suitably also water. Furthermore, the liquid may include fat, preferably in the form of living tissue.

After filling of the cavity in the bone with this bone tissue material it has been tried to laterally compact the paste or pulp by different types of means or a femur stem portion having a larger size than the one to be finally secured be cementing. There has been a considerable difficulty to obtain centering of the final smaller cavity in the middle of the femur. Furthermore, it has been difficult to lead liquid away from the bone tissue material during the compacting. It has also been problematic to achieve a correctly adjusted size and shape of the smaller cavity desired, so that the final prosthesis stem portion to be applied in the cavity gets a homogeneous bone cement casing therearound.

SUMMARY OF THE INVENTION

The object of the present invention is to improve the device and the method of the type described above.

According to a first aspect of the invention it is aimed at making it possible to created the transplant so that the cavity delimited thereby gets a substantially central location in the bone. The expression "substantially central" should here be interpreted as having a comparatively broad meaning; the essential thing is that the resulting cavity is restricted by bone material having such a thickness that the prosthesis portion introducable into the cavity becomes a steady and secure anchorage therein.

According to another aspect of the invention it is aimed at making it possible to efficiently compact the bone tissue material in the cavity by draining excess liquid from the bone tissue material, so that the latter may efficiently consolidate as the compacting proceeds.

The objects according to the invention are obtained by the different characteristics defined in the appended claims.

The desired centering of the compacting means in the cavity in the bone is obtained by using the guide pin according to the invention and the construction of the compacting means with an opening for passage of the guide pin, so that the compacting means will be guided by the guide pin on movement thereof with respect to the guide pin and the bone.

The drainage of the liquid from the bone tissue material is in accordance with the invention achieved by providing the compacting means with a jacket delimiting an inner hollow space and providing the jacket with openings for allowing liquid to pass through the jacket and into the hollow space. The liquid may then be removed from said hollow space by any conventional liquid suction device used within the surgery or other liquid evacuating equipments suitable for this task.

Further advantages and characteristics of the invention will appear from the appended claims and the description below.

BRIEF DESCRIPTION OF THE DRAWINGS

With reference to the appended drawings, below follows a specific description of embodiments of the invention cited as examples.

In the drawings:

FIG. 5 is a schematic and partially sectioned view illustrating a femur with a cavity and an assembly introduced therein, which consists of the guide pin and the centering sleeve according to FIGS. 1 and 2, FIG. 6 is a view similar to FIG. 5 but illustrating the guide pin and the compacting means in the cavity, wherein a bone tissue transplantation material has also been introduced therein, and FIG. 7 is a view similar to FIG. 5 with respect to the femur but illustrating an alternative method for locating the inner end of the guide pin with respect to the bone.

DETAILED DESCRIPTION OF PREFERRED EMBODIMENTS

The device according to the invention such as illustrated in FIGS. 1-6 comprises three members. A first of the members is constituted by the guide pin 1 illustrated in FIG. 1. The second of the members is constituted by the centering means 2 illustrated in FIG. 2. The third of the members is constituted by the compacting means 3 illustrated in FIGS. 3 and 4.

Figure 1:
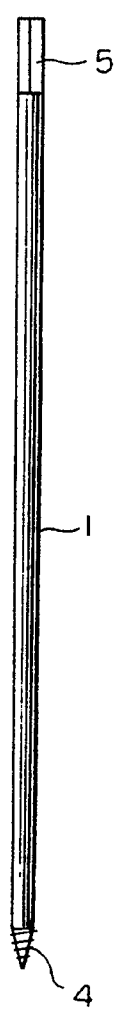
FIG. 1 is a side elevation of a guide pin included in the device according to the invention.
Figure 2:
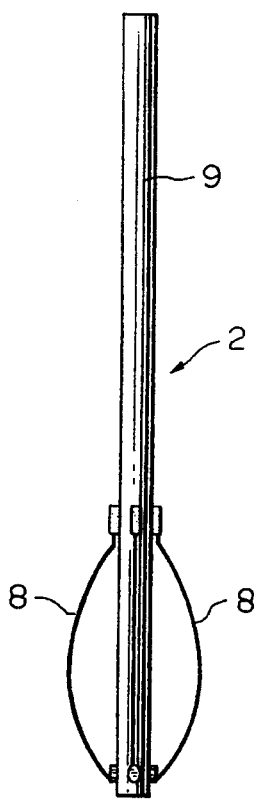
FIG. 2 is a side elevation of a centering sleeve of the device.
Figure 3:
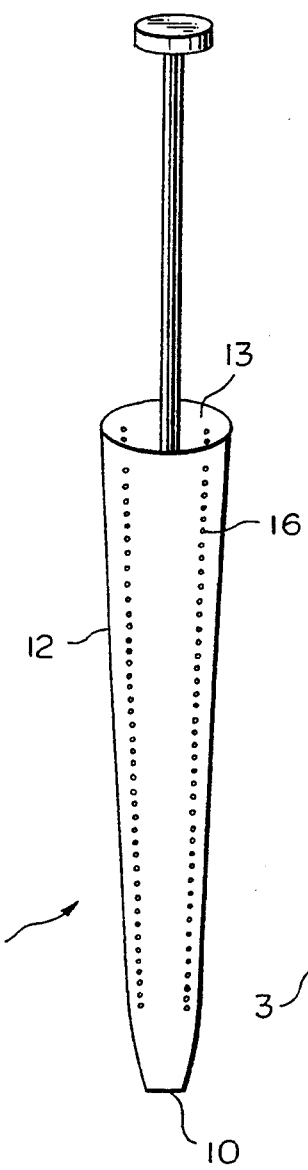
FIG. 3 is a side view of a compacting means included in the device.
Figure 4:
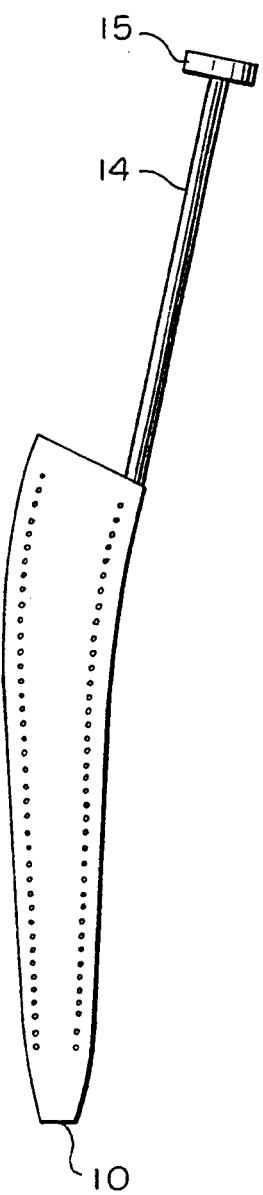
FIG. 4 is a view of the means in FIG. 3 but with the means turned by 90° compared with the position in FIG. 3.

The guide pin 1 according to FIG. 1 is comparatively long and narrow and has at one end thereof a thread 4 for screwing into the bone. The guide pin 1 has at the other end a key grip 5 or the like for facilitating the turning of the guide pin.

The guide pin 1 is adapted to be applied substantially centrally in a cavity 7 present in the bone 6 in question (FIG. 5), especially a femur. The centering means 2 illustrated in FIG. 2 may be used to this end, said centering means being engagable with the guide pin and comprising centering members 8 adapted to carry out the centering by resting on or bearing against the wall of the cavity. The centering member 8 may be designed as compliant, i.e. flexible, arms or wings, for example made by spring steel, so that irregularities of the shape of the cavity 7 may be considered by deformation of the arms or wings.

The centering means 2 comprises also a sleeve 9, through which the guide pin 1 may extend. The centering members 8 are arranged on the outside of the sleeve 9.

The thread 4 applied on the guide pin 1 is preferably conical or otherwise so designed that it becomes of the self-tapping type, i.e. that the same may be threaded into the bone 6 in the bottom of the cavity 7 without any urgent need of preboring.

The compacting means 3 is adapted to act for compacting of the bone tissue material in the cavity 7. The compacting means 3 has an opening 10 (FIGS. 3, 4 and 6) for passage of the guide pin 1 so as to obtain guiding of the compacting means 3 by the guide pin 1 on movement of said means with respect thereto. The essential thing in this case is that said guiding takes place in the inner portion of the cavity 7 in the bone 6, since it is most difficult for the surgeon to control the position of the end of the compacting means located furthest inside the cavity. This means that it may be sufficient to guide the compacting means 3 by the guide pin in the bottom region of the cavity 7, which is also intended in the embodiment example illustrated. The opening 10 receiving the guide pin 1 may for obtaining this be arranged to cooperate guidingly with the guide pin only at that end of the compacting means 3 which in the realisation of the compacting is intended to be located furthest inside the cavity 7. Accordingly, the surgeon has to decide the lateral position of the compacting means 3 in the region of the mouth 11 of the cavity 7 (FIG. 5). However, this does not prevent the compacting means 3 from being constructed so that it, also in one or several places located at a distance from that end which in the active compacting state of the compacting means is intended to be located in the bottom region of the cavity 7, may cooperate mutually guidingly with the guide pin.

The compacting means 3 has a jacket 12 delimiting an inner hollow space 13. The jacket 12 is provided with a great amount of very small openings 16 so as to allow liquid to pass through the jacket and into the hollow space 13.

Expressed in another way, the compacting means 3 may be considered as a sleeve, the shape of which is generally conical or tapering. The guiding opening 10 is located at the most narrow end of the jacket or sleeve 12. A shaft 14 is arranged at the opposite end of the jacket 12 and used when the compacting means is driven down into the bone transplant. The shaft 14 may at its upper end have a strike receiving member 15.

The use of the embodiment according to FIGS. 1-6 is carried out in the following way: the guide pin 1 and the centering sleeve 2 are initially brought down into the cavity 7 in the bone 6 in the way indicated in FIG. 5. The guide pin 1 is then located inside the sleeve 2 and is centered in the cavity thereby. The guide pin 1 is then threaded down into the bone 6, so that it obtains the state according to FIG. 6, in which the guide pin 1 is fixed in the cavity 7. The centering sleeve 2 is then drawn out of the cavity 7. The cavity 7 is then filled to a required extent with bone tissue material to be transplanted therein and this is in FIG. 6 indicated by 15. The compacting means 3 is then threaded onto the guide pin 1 and the compacting means is forced or struck down into the bone transplant, so that this is laterally compacted. Liquid forced away upon the compacting may pass through the openings 16 in the jacket 12 of the compacting means 3 and into the hollow space 13 inside the compacting means. The liquid may be sucked away from this hollow space 13 by a hose or another appliance which is inserted into the hollow space 13 of the compacting means through the upper open end 17 of the hollow space. The procedure is repeated by drawing the compacting means 3 out of the cavity 7, whereupon a new bone transplant is filled into the cavity 7. The compacting means 3 is then again struck down until a sufficiently hard compacting of the bone transplant 15 against the remaining surrounding bone material, which restricted the cavity 7 before the bone transplant was introduced therein, has been obtained. The compacting means 3 is in the final state located approximately in the position according to FIG. 6 and it is then removed. The guide pin 1 is then removed and the cavity, the size and shape of which substantially correspond to the outer shape of the compacting means 3, is then remaining in the bone 6. Accordingly, the bone transplant becomes homogeneously and uniformly compacted over the walls in the cavity in the bone 6 where the stem portions of the previous prosthesis were located.

According to a first variant it is now possible to more or less fill the cavity obtained, which has got a desired shape and a required thickness of the bone material forming the wall of the cavity, by bone cement and the stem portion of a new prosthesis may then be pressed into the cavity and bound to the compacted transplant by means of the bone cement. It appears from above that the stem portion of the new prosthesis is generally designed with dimensions slightly smaller than the compacting means 3 itself, but for the rest with the same shape.

According to another variant suitable in such cases in which it is not possible to immediately apply the new prosthesis because of an infection or a bone being too fragile, it is possible to wait the time required, for instance some weeks, after the very bone transplantation for the prosthesis application. The bone transplant is then applied in the way already described. The cavity obtained thereby is then filled with a filler body having substantially the same dimensions as the compacting means 3. The operation is then terminated and the bone transplant is left to heal or grow together with the surrounding bone for the time required. The filler body is after that removed in a new operation, whereupon the new prosthesis is secured by cementing.

The variant in FIG. 7 does not use the centering sleeve 9 previously described. The centering means 2 is instead constituted by a plug 18. The guide pin comprises some type of means 19 for engagement with the corresponding means 20 of the plug. The means 19, 20 is in the illustrated example indicated to consist of mutually engaging threads. The plug 18 is intended to be located in a bore carried out in the bottom of the cavity 7 in the alternative according to FIG. 7. Accordingly, this bore is carried out so that it is located approximately in the centre of the bone 6, whereupon the plug 18 is introduced into this bore and the guide pin 1 is then brought to lockingly engage into the plug 18. The compacting means 3 may then be threaded over the guiding pin 1 and the bone transplant be compacted in place in the way already described.

A plug 18, which would not be intended to be located in any bore, may according to an alternative to the embodiment illustrated in FIG. 7 be used instead of holding or centering the guide pin 1 in the cavity 7. This alternative plug would instead be provided with centering members adapted to carry out a centering of the plug in the cavity by bearing against the wall of the cavity 7. However, the guide pin 1 and the plug 18 would as in the case according to FIG. 7 have mutually engaging means, so that the plug with said centering members acted so as to maintain the end of the guide pin 1 located furthest inside the cavity 7 approximately centrally in the cavity. The centering members on this plug suitably consist of resilient arms or wings extending outwardly from the plug, as described in connection with the centering sleeve 9. Accordingly, in this alternative the intention is to bring the guide pin 1 out of the engagement with the plug after the application of the bone transplant and draw it out of the cavity while leaving the plug behind in the bottom of the cavity.

It is evident that the invention may be modified in several ways within the scope of the inventional idea.

I claim:

1. A device for use in transplantation of bone tissue material in a cavity of a bone so as to give the cavity a desired shape with a required thickness of the bone material forming a wall of the cavity, said device comprising:

means for compacting the bone tissue material in the cavity, a guide pin for fixed engagement to said bone substantially centrally in the cavity, said compacting means having an opening for passage of the guide pin, said guide pin guiding sliding movement of the compacting means within said cavity when said guide pin is engaged to said bone, wherein the compacting means has a jacket to compact the bone material, said jacket delimiting an inner hollow space and having a plurality of openings to allow liquid to pass through the jacket and into the hollow space when compacting the bone material.

2. A device according to claim 1, which comprises means for centering the guide pin in the cavity.

3. A device according to claim 2, wherein the centering means is engagable with the guide pin and comprises centering member means for bearing against the wall of the cavity.

4. A device according to claim 3, wherein said centering members are made as compliant arms.

5. A device according to claim 2, wherein the centering means comprises a sleeve, through which the guide pin may extend.

6. A device according to claim 1, wherein the guide pin comprises a thread for screwing thereof into the bone.

7. A device according to claim 2, wherein the guide pin comprises means for engagement with a plug forming said centering means.

8. A device for use in transplantation of bone tissue in a cavity of a bone so as to give the cavity a desired shape with a required thickness of the bone material forming a wall of the cavity, said device comprising means for compacting the bone tissue material in the cavity, wherein the compacting means has a jacket to compact the bone material, said jacket delimiting an inner hollow space and having openings to allow liquid from the surrounding bone tissue material to pass through the jacket and into the hollow space.

9. A method for use in transplantation of bone tissue material in a cavity of a bone so as to give the cavity a desired shape with a required thickness of the bone material forming a wall of the cavity, said bone tissue material being compacted in the cavity against remaining bone material by means of a compacting means, wherein during compacting liquid from the surrounding bone tissue material is allowed to flow into an inner hollow space delimited by a jacket of the compacting means through openings in the jacket wherein liquid contained within said hollow space can thereafter be removed.

* * * * *